(12) United States Patent
Sgroi, Jr.

(10) Patent No.: US 11,058,429 B2
(45) Date of Patent: Jul. 13, 2021

(54) LOAD SENSING ASSEMBLIES AND METHODS OF MANUFACTURING LOAD SENSING ASSEMBLIES

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 141 days.

(21) Appl. No.: 16/449,813

(22) Filed: Jun. 24, 2019

(65) Prior Publication Data
US 2020/0397440 A1 Dec. 24, 2020

(51) Int. Cl.
*A61B 17/115* (2006.01)
*A61L 31/06* (2006.01)
*A61B 90/00* (2016.01)
*A61B 17/00* (2006.01)
*A61B 17/072* (2006.01)

(52) U.S. Cl.
CPC .......... *A61B 17/1155* (2013.01); *A61L 31/06* (2013.01); *A61B 2017/00526* (2013.01); *A61B 2017/07257* (2013.01); *A61B 2017/07271* (2013.01); *A61B 2017/07285* (2013.01); *A61B 2090/064* (2016.02)

(58) Field of Classification Search
CPC ... A61L 31/06; G01J 5/10; G01J 5/061; G01J 5/041; G01J 5/046; G01J 5/048
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,869,719 A | 9/1989 | Hogan |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

European Search Report dated Nov. 24, 2020, issued in corresponding EP Appln. No. 20180352, 6 pages.

*Primary Examiner* — Nathaniel C Chukwurah (57) ABSTRACT

An adapter assembly of a circular stapling instrument includes a load sensing assembly configured to measure a load exerted on a tubular housing of the adapter assembly. The load sensor assembly has a sensor body, electrical components supported by the sensor body, and a hermetic seal assembly enclosing the electrical components. The hermetic seal assembly includes a stamped base portion and an overmolded upper portion.

9 Claims, 6 Drawing Sheets

(56) References Cited

U.S. PATENT DOCUMENTS

| | | |
|---|---|---|
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,968,012 A | 10/1999 | Ren et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,197,002 B1 | 3/2001 | Peterson |
| 6,221,023 B1 | 4/2001 | Matsuba et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B2 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,692,482 B2 | 2/2004 | Heller et al. |
| 6,698,643 B2 | 3/2004 | Whitman |
| 6,699,177 B1 | 3/2004 | Wang et al. |
| 6,706,018 B2 | 3/2004 | Westlund et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,094,220 B2 | 8/2006 | Tanghoj et al. |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,731,707 B2 | 6/2010 | Heller et al. |
| 7,738,971 B2 | 6/2010 | Swayze et al. |
| 7,740,159 B2 | 6/2010 | Shelton, IV et al. |

(56) References Cited

U.S. PATENT DOCUMENTS

| | | |
|---|---|---|
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,798,999 B2 | 9/2010 | Bailey et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,854,727 B2 | 12/2010 | Belsley |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,988,699 B2 | 8/2011 | Martz et al. |
| 7,992,758 B2 | 8/2011 | Whitman et al. |
| 8,016,178 B2 | 9/2011 | Olson et al. |
| 8,016,752 B2 | 9/2011 | Armstrong et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,025,621 B2 | 9/2011 | Ewaschuk et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,292,963 B2 | 10/2012 | Miller et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,444,625 B2 | 5/2013 | Stalker et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,987,095 B2 | 6/2018 | Chowaniec et al. |
| 2001/0031975 A1 | 10/2001 | Whitman et al. |
| 2001/0034501 A1 | 10/2001 | Tom |
| 2002/0049454 A1 | 4/2002 | Whitman et al. |
| 2002/0128607 A1 | 9/2002 | Haury et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2004/0260246 A1 | 12/2004 | Desmond |
| 2005/0004553 A1 | 1/2005 | Douk |
| 2005/0075711 A1 | 4/2005 | Neary |
| 2005/0096507 A1 | 5/2005 | Prosek |
| 2005/0131390 A1 | 6/2005 | Heinrich et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0200185 A1 | 9/2006 | Marchek et al. |
| 2006/0229573 A1 | 10/2006 | Lamborne |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0151390 A1 | 7/2007 | Blumenkranz et al. |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |

(56) References Cited

U.S. PATENT DOCUMENTS

| | | |
|---|---|---|
| 2009/0099876 A1 | 4/2009 | Whitman |
| 2009/0138006 A1 | 5/2009 | Bales et al. |
| 2009/0157092 A1 | 6/2009 | Blumenkranz et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0174327 A1 | 7/2010 | Radermacher |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228233 A1 | 9/2010 | Kahn |
| 2010/0312257 A1 | 12/2010 | Aranyi |
| 2011/0071508 A1 | 3/2011 | Duval et al. |
| 2011/0077673 A1 | 3/2011 | Grubac et al. |
| 2011/0118577 A1 | 5/2011 | Pfeiffer et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184406 A1 | 7/2011 | Selkee |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016402 A1 | 1/2012 | Weisshaupt et al. |
| 2012/0046577 A1 | 2/2012 | Soltz |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116248 A1 | 5/2012 | McWeeney et al. |
| 2012/0116368 A1 | 5/2012 | Viola |
| 2012/0123389 A1 | 5/2012 | Shafran |
| 2012/0143002 A1 | 6/2012 | Aranyi et al. |
| 2012/0150063 A1 | 6/2012 | Rea |
| 2012/0172924 A1 | 7/2012 | Allen, IV |
| 2012/0223121 A1 | 9/2012 | Viola et al. |
| 2012/0245426 A1 | 9/2012 | Salvas et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323081 A1 | 12/2012 | Son |
| 2012/0323226 A1 | 12/2012 | Chowaniec et al. |
| 2012/0330285 A1 | 12/2012 | Hartoumbekis et al. |
| 2013/0012983 A1 | 1/2013 | Kleyman |
| 2013/0018361 A1 | 1/2013 | Bryant |
| 2013/0053782 A1 | 2/2013 | Shelton, IV |
| 2013/0090531 A1 | 4/2013 | Ryan |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0110085 A1 | 5/2013 | Adamson |
| 2013/0165942 A1 | 6/2013 | Tan-Malecki et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0220345 A1 | 8/2013 | Allphin et al. |
| 2013/0237950 A1 | 9/2013 | Gianotti et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0263561 A1 | 9/2014 | Castro |
| 2014/0276932 A1 | 9/2014 | Williams et al. |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2018/0266888 A1 | 9/2018 | Maston |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1974676 A1 | 10/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |

(56) References Cited

FOREIGN PATENT DOCUMENTS

| | | | |
|---|---|---|---|
| EP | 2606834 | A2 | 6/2013 |
| EP | 2668910 | A2 | 12/2013 |
| EP | 2676615 | A2 | 12/2013 |
| EP | 2881046 | A2 | 6/2015 |
| EP | 3293503 | A1 | 3/2018 |
| EP | 3318212 | A1 | 5/2018 |
| EP | 3403592 | A1 | 11/2018 |
| ES | 2333509 | A1 | 2/2010 |
| JP | 08038488 | | 2/1996 |
| JP | 2005125075 | A | 5/2005 |
| KR | 20120022521 | A | 3/2012 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 0030743 | A2 | 4/2003 |
| WO | 03026511 | A1 | 4/2003 |
| WO | 03065916 | A1 | 8/2003 |
| WO | 03077769 | A1 | 9/2003 |
| WO | 03090630 | A2 | 11/2003 |
| WO | 2004107989 | A1 | 12/2004 |
| WO | 2006042210 | A2 | 4/2006 |
| WO | 2007016290 | A2 | 2/2007 |
| WO | 2007026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |
| WO | 2009143092 | A1 | 11/2009 |
| WO | 2009149234 | A1 | 12/2009 |
| WO | 2010030114 | A2 | 3/2010 |
| WO | 2011108840 | A2 | 9/2011 |
| WO | 2012040984 | A1 | 4/2012 |

LOAD SENSING ASSEMBLIES AND METHODS OF MANUFACTURING LOAD SENSING ASSEMBLIES

BACKGROUND

1. Technical Field

The disclosure relates to surgical devices. More specifically, the disclosure relates to handheld electromechanical circular stapling instruments for performing end-to-end anastomosis procedures.

2. Background of Related Art

Circular clamping, cutting and stapling devices may be employed in a surgical procedure to reattach colon portions that were previously transected, or to conduct similar procedures. Conventional circular clamping, cutting, and stapling devices include a pistol or linear grip-styled structure having an elongated shaft extending therefrom and a loading unit portion. The loading unit portion includes an end effector having a staple cartridge housing a plurality of staples supported on the distal end of the elongated shaft and an anvil assembly supported adjacent to the staple cartridge. During the surgical procedure, a physician may insert the loading unit portion of the circular stapling device into a rectum of a patient and maneuver the device up the colonic tract of the patient toward the transected colon portions. The anvil assembly can be purse stringed along one of the transected colon portions. Alternatively, if desired, the anvil assembly can be inserted into the colon through an incision proximal to the transected colon portion. Once properly positioned within the transected colon portions, the anvil assembly and staple cartridge are approximated toward one another and the staples are ejected from the staple cartridge toward the anvil assembly thereby forming the staples in tissue to affect an end-to-end anastomosis of the transected colon portions. An annular knife is fired to core the anastomosed colon portions. After the end-to-end anastomosis has been affected, the circular stapling device is removed from the surgical site.

The circular clamping, cutting, and stapling devices may include a powered drive system including a powered handle assembly, which may be reusable, and a disposable end effector that is removably connected to the powered handle assembly.

Many of existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use a rotary driving force.

In order to make the linear driven end effectors compatible with powered surgical devices that use a rotary driving force, adapters are used to interconnect the linear driven end effectors with the powered rotary driven surgical devices. These adapters may also be reusable, and as such, are configured to withstand multiple sterilization cycles. Prior to undergoing a sterilization process, certain components of the adapter may be removed to allow access of sterilization fluids into areas of the adapter and/or to prevent damage to vulnerable components of the adapter.

SUMMARY

Powered surgical devices may include various sensors for providing feedback during their operation. However, one limitation of the electronics and sensors used in the sterile environment of the operating room is that they need to be designed to withstand multiple cleaning and autoclave cycles. In order to gather information of the mechanical forces applied by the powered surgical devices, load sensing devices, such as load cells, are disposed on one or more mechanical components of the powered surgical device and/or adapters coupled thereto.

According to one embodiment of the disclosure, a load sensing assembly for a circular stapler is provided and includes a sensor body defining a pocket therein, a load sensor circuit disposed within the pocket and coupled to the sensor body, and a hermetic seal assembly enclosing the load sensor circuit therein. The hermetic seal assembly includes a base portion configured to be received in the pocket, and a cover overmolded to the base portion.

In aspects, the base portion may be formed by short run stamping.

In aspects, the base portion may be fabricated from metal and the cover may be fabricated from plastic.

In aspects, the cover may define a cavity therein.

In aspects, the load sensing assembly may further include a signal processing circuit disposed within the cavity of the cover and electrically coupled to the load sensor circuit.

In aspects, the base portion has a flange extending outwardly therefrom, the flange being supported in the pocket.

In aspects, the cover may have a bottom end portion overmolded around an outer surface of the base portion.

In aspects, the base portion may define a series of holes disposed around an upper end portion of the base portion.

In aspects, the cover may be fabricated from a liquid crystal polymer, polyether ether ketone, polyphenylsulfone, polyphenylene oxide, polyphenylene ether, and/or polyphthalamide.

In accordance with another aspect of the disclosure, a method of manufacturing a load sensing assembly is provided. The method includes short run stamping a base portion of a hermetic seal assembly, overmolding a cover of the hermetic seal assembly to the base portion, positioning a load sensor circuit within a pocket defined in a sensor body, and enclosing the load sensor circuit in the hermetic seal assembly.

In aspects, the base portion may be fabricated from metal and the cover may be fabricated from plastic.

In aspects, the method may further include positioning a signal processing circuit within a cavity defined in the cover, and electrically coupling the signal processing circuit to the load sensor circuit.

In aspects, the method may further include positioning the base portion in the pocket.

In aspects, positioning the base portion in the pocket may include positioning a flange that extends outwardly from the base portion into the pocket.

In aspects, overmolding the cover to the base portion may include overmolding a bottom end portion of the cover around an outer surface of the base portion.

In aspects, the method may further include forming a series of holes around an upper end portion of the base portion prior to overmolding the cover to the base portion.

In aspects, the cover may be fabricated from a liquid crystal polymer, polyether ether ketone, polyphenylsulfone, polyphenylene oxide, polyphenylene ether, and/or polyphthalamide.

In accordance with yet another aspect of the disclosure, a hermetic seal assembly for a sensor is provided. The hermetic seal assembly includes a base portion and a cover overmolded to the base portion. The base portion is fabricated from a first material configured to be weld compatible, and the cover is fabricated from a second material.

In aspects, the first material of the base portion may be metal and the second material of the cover may be plastic.

In aspects, the cover may define a cavity therein and may have a bottom end portion overmolded around an outer surface of the base portion.

BRIEF DESCRIPTION OF THE DRAWINGS

Embodiments of the disclosure are described herein with reference to the accompanying drawings, wherein.

DETAILED DESCRIPTION OF EMBODIMENTS

Embodiments of the disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the disclosure in unnecessary detail.

The disclosure relates to powered surgical devices having electronic sensors for monitoring mechanical strain and forces imparted on components of the powered surgical devices. More particularly, this disclosure relates to load measuring sensors including load sensing devices as well as analog and digital circuitry that are hermetically sealed such that the load sensors are configured to resist harsh environments. The load sensors are hermetically sealed in a hermetic seal assembly manufactured by short run stamping a base portion and then overmolding a cover to the base portion, thereby forming an enclosure for the load sensors. The manufacturing of the hermetic seal assembly is simple, cheap, highly tolerant, and results in a hermetic seal assembly that effectively shields the load sensors during a sterilization process.

Figure 1:
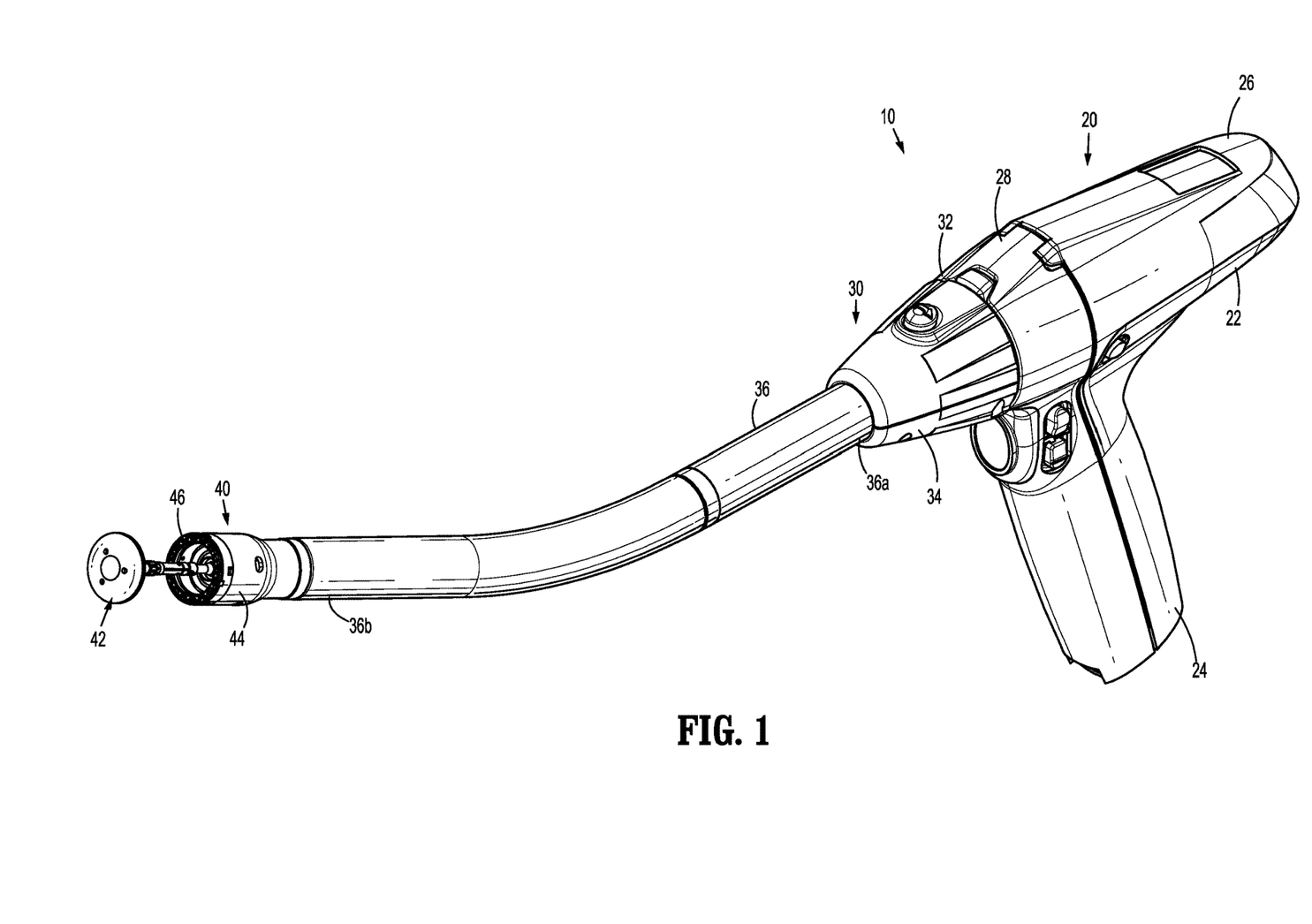
FIG. 1 is a perspective view illustrating a handheld surgical stapling instrument including a powered handle assembly, an adapter assembly, and an end effector having a reload and an anvil assembly according to an exemplary embodiment of the disclosure.
Figure 2:
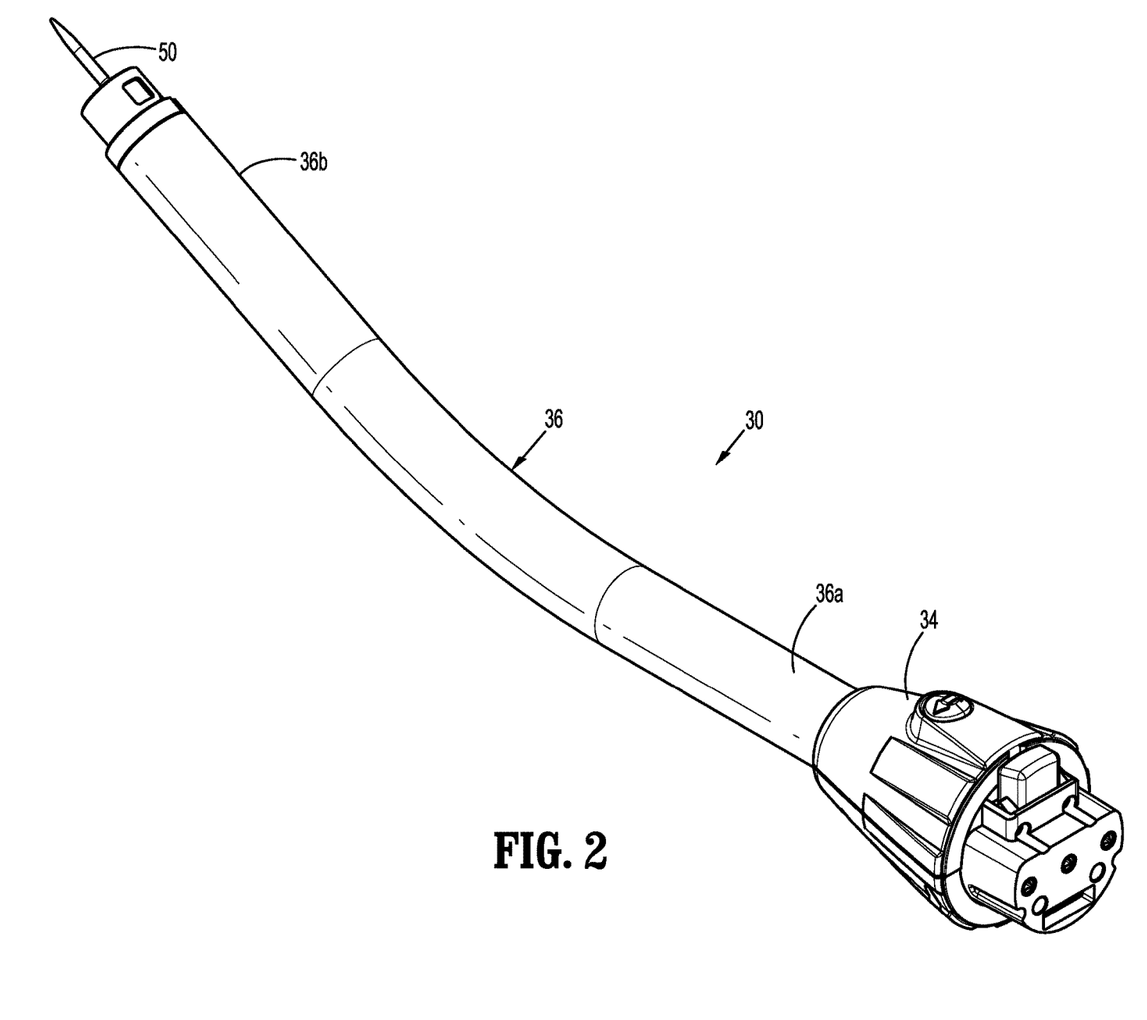
FIG. 2 is a perspective view illustrating a trocar assembly disposed with the adapter assembly of FIG. 1.
Figure 3:
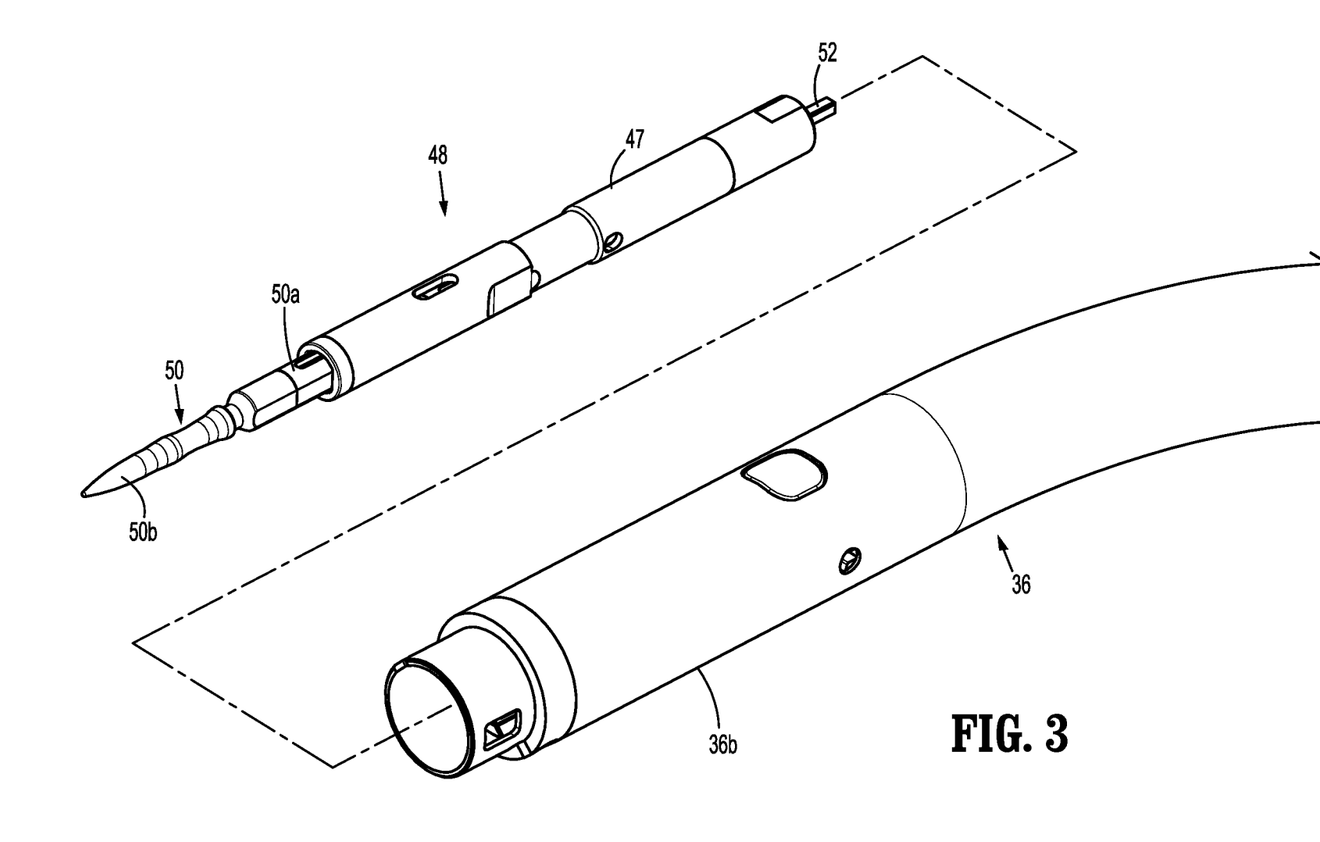
FIG. 3 is a perspective view, with parts separated, of the trocar assembly of FIG. 2 being assembled to a tubular housing of the adapter assembly.

With reference to FIGS. 1-3, a powered surgical device, such as, for example, a circular stapler 10, includes a powered handle assembly 20, which is configured for selective connection with an adapter assembly 30, which in turn, is configured for selective connection with an end effector, such as an annular reload 40. Although generally referred to as being a powered surgical device, it is contemplated that the surgical device 10 may be a manually actuated and may include various configurations.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. The upper housing portion 28 has a distal portion 32 that is configured to accept a proximal housing portion 34 of the adapter assembly 30.

The adapter assembly 30 includes a tubular housing 36 that extends between a proximal end portion 36a extending distally from the proximal housing portion 34 and an opposite, distal end portion 36b that is configured for operable connection to the reload 40. The adapter assembly 30 is configured to convert a rotational motion provided by the handle assembly 20 into axial translation useful for advancing/retracting a trocar member 50 of a trocar assembly 48 (FIG. 3) slidably disposed within the distal end portion 36b of the tubular housing 36 of the adapter assembly 30 for firing staples of the reload 40.

FIG. 3 illustrates the trocar assembly 48 which includes a trocar housing 47, a trocar lead screw 48, and a trocar member 50. The trocar member 50 extends distally beyond the distal end portion 36b of the tubular housing 36. The trocar member 50 includes a proximal end portion 50a coupled to the lead screw 52 of the trocar assembly 48, and a distal end portion 50b configured to selectively engage an anvil assembly 42. The lead screw 52 may be threadedly coupled to the trocar member 50, such that a rotation of the lead screw 52 results in an axial translation of the trocar member 50. When the anvil assembly 42 (FIG. 1) is connected to the trocar member 50, axial translation of the trocar member 50 in a first direction results in an opening of the anvil assembly 42 relative to the reload 40, and axial translation of the trocar member 50 in a second, opposite direction, results in a closing of the anvil assembly 42 relative to the reload 40 to capture tissue therebetween.

As best shown in FIG. 1, the reload 40 includes a housing 44 and a staple cartridge 46 fixedly secured to a distal end portion of the housing 44. The housing 44 is configured for selective connection to the distal end portion 36b of the tubular housing 36 of the adapter assembly 30. The reload 40 is configured to fire and form an annular array of surgical staples against the anvil assembly 42, and to sever a ring of tissue.

For a detailed description of an exemplary powered surgical stapler including an adapter assembly and a reload, reference may be made to commonly owned U.S. Patent Application Publication No. 2016/0310134 by Contini et al., titled "Handheld Electromechanical Surgical System," filed Apr. 12, 2016.

Figure 4:
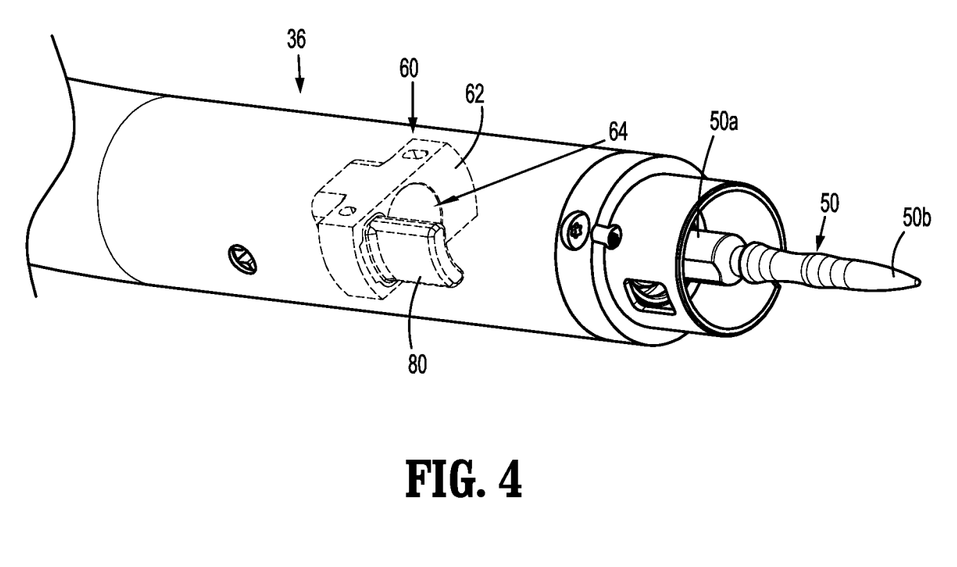
FIG. 4 is a perspective view illustrating a load sensing assembly, shown in phantom, supported within the tubular housing of the adapter assembly shown in FIG. 1.

FIG. 4 illustrates the adapter assembly 30 which includes a load sensing assembly 60 disposed within the tubular housing 36 that is configured for electrical connection with and between the handle assembly 20 and the reload 40. The load sensing assembly 60 provides for communication (e.g., identifying data, life-cycle data, system data, load sense signals) with a main controller (not shown) of the handle assembly 20. The load sensing assembly 60 also provides strain measurements imparted on the adapter assembly 30 during movement of the trocar member 50 when coupled to the anvil assembly 42 during clamping, stapling, cutting, and other mechanical actuations.

Figure 5:
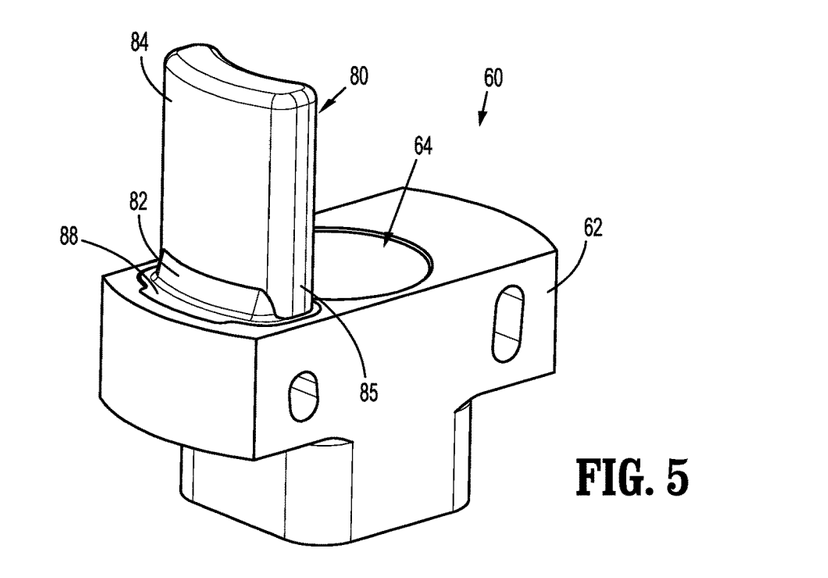
FIG. 5 is a perspective view illustrating the load sensing assembly of FIG. 4.
Figure 6:
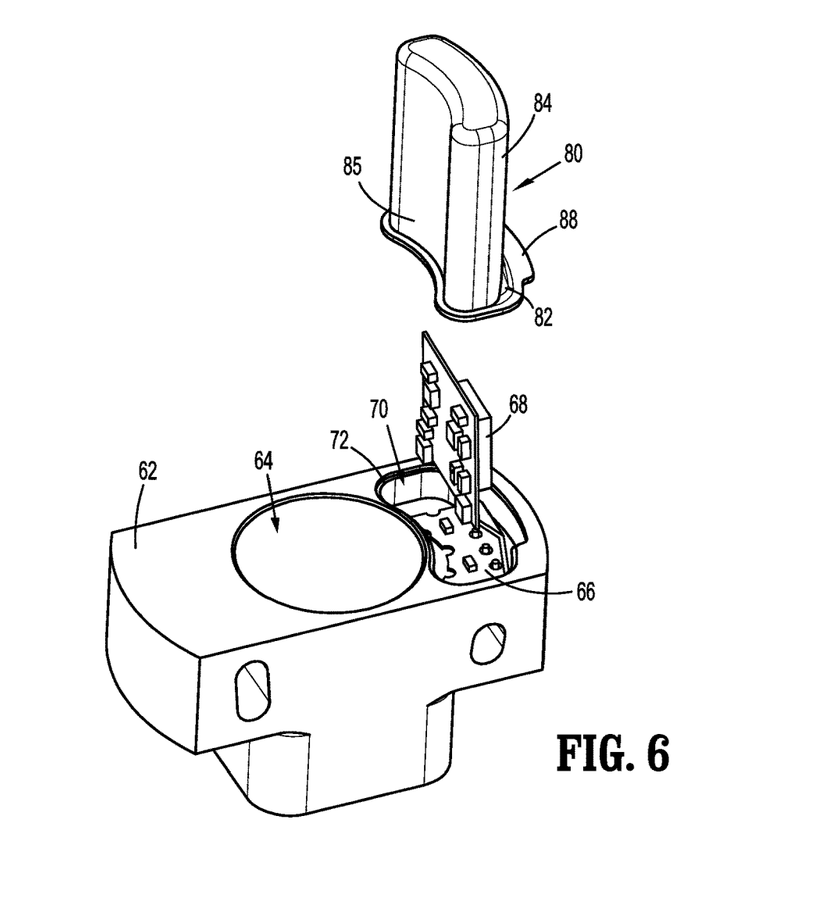
FIG. 6 is a perspective view, with parts separated, of the load sensing assembly of FIG. 5 illustrating internal electrical components and a hermetic seal assembly of the load sensing assembly.

FIGS. 4-6 illustrate the load sensing assembly 60 which includes a sensor body 62 and a hermetic seal assembly 80 for sealing electrical components with the sensor body 62. The sensor body 62 defines a passageway 64 configured for slidable movement of the trocar assembly 48 (e.g., the trocar member 50). The sensor body 62 may be formed from any suitable material, such as stainless steel, that allows for the sensor body 62 to be elastically deformed when stressed. In embodiments, the sensor body 62 may be fabricated from stainless steel, such as 17-4 stainless steel heat-treated to H-900 standard. The electrical components of the load sensing assembly 60 include a load sensor circuit 66 disposed within a pocket 70 (FIG. 6) defined in the sensor body 62 and a signal processing unit 68 electromechanically coupled to the load sensor circuit 66 and received within the hermetic seal assembly 80.

The design of the sensor body 62 allows for uniform bending when loaded. The uniform loading and resulting strain output causes the load sensor circuit 66 of the load sensing assembly 60 to provide linear strain output of the sensor body 62. The signal processing circuit 68 includes analog and digital circuit components (e.g., a controller) that are configured to perform signal processing on signals from the load sensor circuit 66 and output a measurement signal to the handle assembly 20. During operation of the surgical device 10, namely, clamping, stapling, and cutting, the sensor body 62 is elastically deformed (similar to a support beam). In particular, deflection of the sensor body 62 applies a force to the load sensor circuit 66, which is deformed causing its electrical resistance to increase, which is reflected in its measurement signal. A change in a baseline of the measurement signal is indicative of the forces being encountered during clamping, stapling, and cutting.

For a more detailed description of the construction and operation of the electrical components of the loading sensing assembly 60, reference may be made to U.S. Provisional Application No. 62/801,979, filed on Feb. 6, 2019.

FIGS. 5-8 illustrate the hermetic seal assembly 80 of the load sensing assembly 60 which seals the electrical components (e.g., the load sensor circuit 66 and the signal processing unit 68) to shield the electrical components from damage during use of the adapter assembly 30 and during sterilization of the adapter assembly 30. The hermetic seal assembly 80 includes a base portion 82 received in the pocket 70 of the sensor body 62, and a cover 84 overmolded to the base portion 82.

Figure 7:
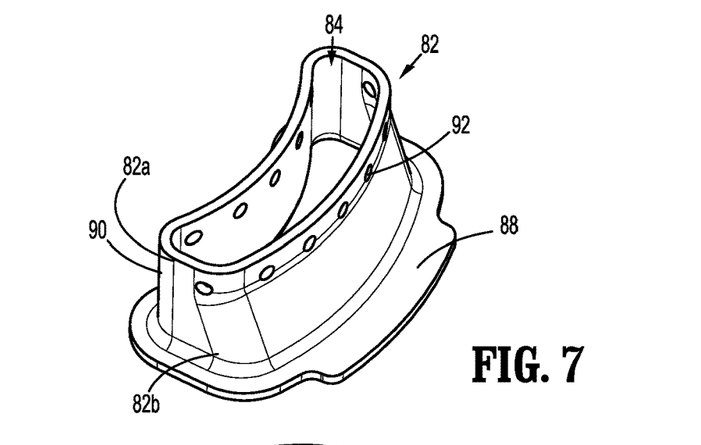
FIG. 7 is a perspective view illustrating a base portion of the hermetic seal assembly prior to completion of a manufacture of the hermetic seal assembly.
Figure 8:
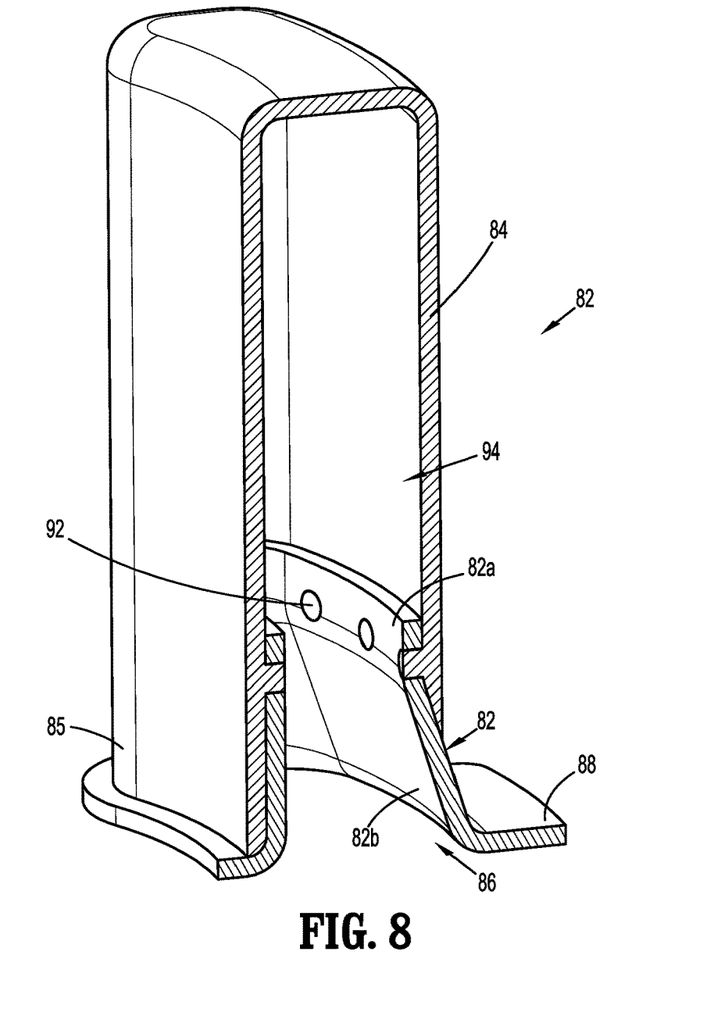
FIG. 8 is a cross-sectional view illustrating the hermetic seal assembly of FIG. 6.

The base portion 82 is fabricated from a metal (e.g., stainless steel) and is formed by short run stamping. In aspects, the base portion 82 may be machined using any suitable material. The base portion 82 has an upper end portion 82a and a lower end portion 82b each defining an opening 84, 86. The lower end portion 82b of the base portion 82 has a flange 88 extending outwardly therefrom. The flange 88 is configured to be supported on a correspondingly shaped seat 72 in the pocket 70 of the sensor body 62. The upper end portion 82b has an outer surface 90 that defines a series of holes 92 disposed around the upper end portion 82b. In some aspects, the outer surface 90 may be devoid of holes 92. The holes 92 facilitate securement of the cover 84 to the base portion 82 during overmolding.

The cover 84 is fabricated from plastic and has a bottom end portion 85 overmolded around the base portion 82. The cover may be fabricated from any material suitable for use in overmolding, such as, for example, a liquid crystal polymer, polyether ether ketone, polyphenylsulfone, polyphenylene oxide, polyphenylene ether, and/or polyphthalamide. The cover 84 defines a cavity 94 therein configured for receipt of the signal processing circuit 68.

To manufacture the hermetic seal assembly 80, the base portion 82 is fabricated by short run stamping a sheet of metal and forming the series of holes 92 in the upper end portion 82a thereof. The base portion 82 is placed in a plastic injection mold and inserted over a complimentary-shaped core to hold the base portion 82 in place. The cover 84 is overmolded around the base portion 82, thereby securing the cover 84 to the base portion 82 and forming an enclosure.

The signal processing circuit 68 is electromechanically coupled to the load sensor circuit 66 and the load sensor circuit 66 is received within the pocket 70 of the sensor body 62. The hermetic seal assembly 80 is attached to the sensor body 62 by affixing the flange 88 of the base portion 82 to the step 72 of the sensor body 62 using a laser weld. Other suitable mechanisms for fastening the hermetic seal assembly 80 to the sensor body 62 are also contemplated, such as adhesives, friction-fit engagements, or the like. Upon positioning the hermetic seal assembly 80 on the sensor body 62, the load sensor circuit 66 is enclosed between the hermetic seal assembly 80 and the sensor body 62, and the signal processing circuit 68 is positioned within the cavity 94 defined in the cover 84.

It will be understood that various modifications may be made to the embodiments of the disclosed adapter assemblies. Therefore, the above description should not be construed as limiting, but merely as exemplifications of embodiments. Those skilled in the art will envision other modifications within the scope and spirit of the disclosure.

What is claimed is:

1. A load sensing assembly for a circular stapler, the load sensing assembly comprising:
    a sensor body defining a pocket therein;
    a load sensor circuit disposed within the pocket and coupled to the sensor body; and
    a hermetic seal assembly enclosing the load sensor circuit therein, wherein the hermetic seal assembly includes:
        a base portion configured to be received in the pocket; and
        a cover overmolded to the base portion.

2. The load sensing assembly according to claim 1, wherein the base portion is formed by short run stamping.

3. The load sensing assembly according to claim 1, wherein the base portion is fabricated from metal and the cover is fabricated from plastic.

4. The load sensing assembly according to claim 1, wherein the cover defines a cavity therein.

5. The load sensing assembly according to claim 4, further comprising a signal processing circuit disposed within the cavity of the cover and electrically coupled to the load sensor circuit.

6. The load sensing assembly according to claim 1, wherein the base portion has a flange extending outwardly therefrom, the flange being supported in the pocket.

7. The load sensing assembly according to claim 1, wherein the cover has a bottom end portion overmolded around an outer surface of the base portion.

8. The load sensing assembly according to claim 1, wherein the base portion defines a series of holes disposed around an upper end portion of the base portion.

9. The load sensing assembly according to claim 1, wherein the cover is fabricated from at least one of a liquid crystal polymer, polyether ether ketone, polyphenylsulfone, polyphenylene oxide, polyphenylene ether, or polyphthalamide.

* * * * *